Figure 1:
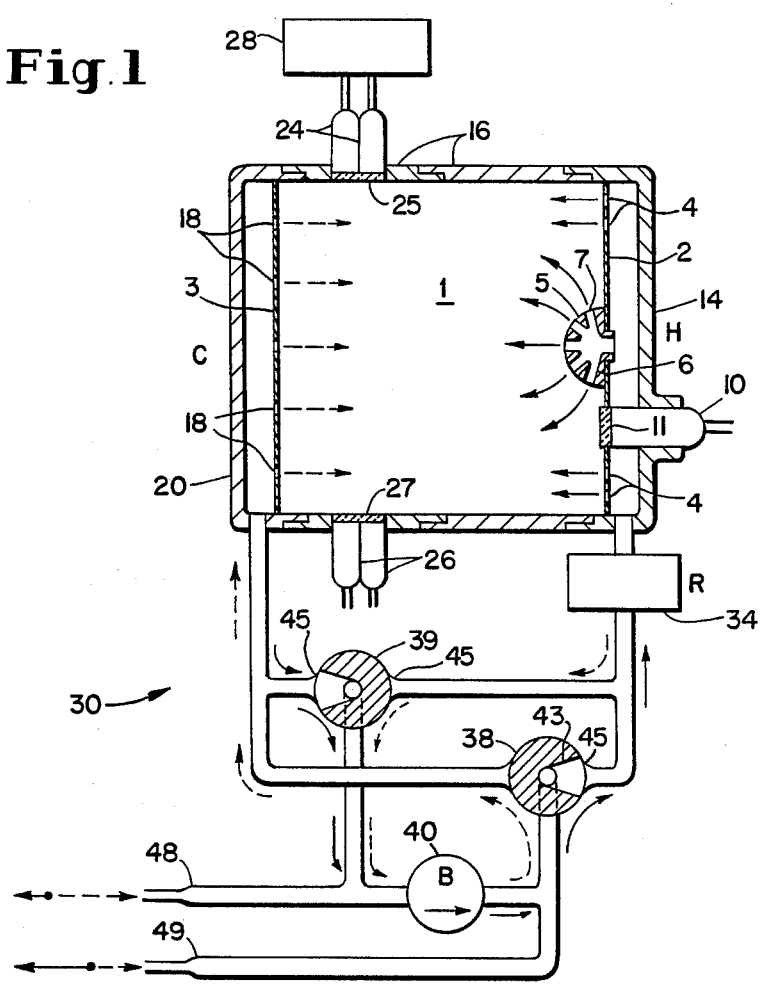

United States Patent [19]

Schuman

[11] Patent Number: 4,711,571
[45] Date of Patent: Dec. 8, 1987

[54] RADIANT EMISSION AND ABSORPTION MULTIGAS ANALYZER

[76] Inventor: Mark Schuman, 101 G St. SW. #516, Washington, D.C. 20024

[21] Appl. No.: 28,026

[22] Filed: Mar. 16, 1987

Related U.S. Application Data

[63] Continuation of Ser. No. 818,919, Jan. 15, 1986, abandoned, which is a continuation of Ser. No. 675,474, Nov. 29, 1984, abandoned, which is a continuation of Ser. No. 416,677, Sep. 10, 1982, abandoned.

[51] Int. Cl.$^4$ .................. G01J 3/443; G01N 21/62
[52] U.S. Cl. ........................... 356/311; 250/343; 250/351; 356/51; 356/417
[58] Field of Search .............. 356/51, 311, 417; 250/343, 351, 352

[56] References Cited

U.S. PATENT DOCUMENTS 3,827,675  8/1974  Schuman ........................... 356/311
3,836,255  9/1974  Schuman ........................... 356/311

*Primary Examiner*—F. L. Evans

[57] ABSTRACT

A spectrometric multigas analyzer is disclosed utilizing substantially isobaric temperature modulation of a gaseous sample in a highly reflective, random path, optical cavity or chamber. Multiple hot and cold ports on opposite sides of the chamber, and a gas recirculation circuit including a heating chamber, thermal regenerator, and cooling chamber, facilitate the alternate replacement of hot gas with cold gas and cold gas with hot gas in the optical chamber each cycle at a frequency of at least several Hertz, thereby producing, by gases of interest in the sample, a modulated spectral infrared emission and a modulated spectral radiant absorption of radiance from a radiant source shining into the optical chamber, which radiant source also provides heat for the heating chamber. For each substance of interest in the gaseous fluid sample, a pair of radiance detectors looking through a pair of optical filters monitor the combined modulated emission/modulated absorption signal from that substance in the optical chamber, whereby its concentration in the sample can be monitored. The temperature modulation also produces a small pressure modulation in a room or building surrounding the device, and certain actions by intruders can cause detectable changes in pressure modulation amplitudes in chambers of the building, which can be monitored by pressure sensors. Thus the device can be used for detecting and monitoring gases, vapors, aerosols, particulates and intruders, e.g., as a combined burglar, fire, and toxic gas alarm.

156 Claims, 4 Drawing Figures

U.S. Patent  Dec. 8, 1987  Sheet 1 of 1  4,711,571

RADIANT EMISSION AND ABSORPTION MULTIGAS ANALYZER

This is a continuation of my patent application Ser. No. 818,919 filed Jan. 15, 1986, which was a continuation of my patent application Ser. No. 675,474 filed Nov. 29, 1984, which was a continuation of my patent application Ser. No. 416,677 filed Sept. 10, 1982, the latter three now abandoned.

The present invention relates generally to spectrometric detection or monitoring the concentration of constituents or substances of interest in the air or other fluid medium, and more particularly to infrared and ultraviolet point sampling devices, which draw into the instrument, from a point in space, a sample of a gas or other fluid or gaseous mixture for analysis.

The closest prior art appears to be my U.S. Pat. No. 3,827,675 entitled "Oscillating Bellows" and my U.S. Pat. No. 3,836,255 entitled "Spectrometric Substance Analyzer Employing Temperature Modulation."

Like the latter patent, the present invention maintains a substantially constant pressure in the optical chamber and utilizes blower and motor-driven valve means, along with external heating and cooling means, to recirculate fluid back to the optical chamber to accomplish the modulation of the temperature of the gaseous fluid in the optical chamber at substantially constant pressure, thereby producing cyclical radiant emission, primarily in the infrared, as a result of temperature modulation of a substance of interestion the fluid in the optical chamber, and cyclical radiant absorption, in the infrared and in other regions of the electromagnetic spectrum according to the output of radiant sources shining into the optical cavity, as a result of the concentration modulation of the substance of interest (concentration varies inversely with the temperature at constant pressure). Since the radiant emission and absorption signals are about 180° out of phase but of opposite polarity, they add rather than tending to cancel each other, at any given wavelength, and the resulting augmented cyclical radiance in the optical chamber or cavity is monitored at wavelengths of interest by radiant detectors (one or more) looking into the optical cavity, utilizing techniques such as synchronous detection (see also my U.S. Pat. No. 3,516,745), whereby the concentrations of many substances or gases of interest may be monitored simultaneously and displayed in real time or recorded. The optical cavity walls always provide the cavity with some infrared radiation, which can be cyclically absorbed by a gas of interest. The motor-driven recirculation means facilitates more stable operation than do the thermally driven bellows and piston of my U.S. Pat. Nos. 3,827,675 and 3,516,745, respectively, and the constant fluid pressure feature, which produces radiant emission and absorption signals, which add algebraically as well as merely vectorially, facilitates operation at greater sensitivity over a broad spectral range than do the bellows and free piston devices, in a practical size gas analyzer.

The present invention differs from the gas analyzer of my U.S. Pat. No. 3,836,255 by more efficient modulation of the fluid temperature in the optical cavity, thereby facilitating greater sensitivity and frequency capability and less power required by the blower and the external heating and cooling means.

Basically these features and performance characteristics are provided, in the present invention, by an optical cavity highly reflective (on the inner surfaces of the walls of a substantially closed chamber) to electromagnetic radiation, e.g., infrared, visible, ultraviolet. The cavity includes first and second wall surfaces (more than two is also possible) pervious to fluid flow into and back out of the cavity via ports in the surfaces. The fluid recirculation means injects hot fluid (e.g., a portion of a gas sample to be analyzed) into the cavity through one of the surfaces while withdrawing cool fluid from the cavity through the other surface and recycling most of the cool fluid right back to the cavity as hot fluid injected through the one surface, by means of a blower or pump, motor-driven valves, a thermal regenerator which releases previously stored heat to the cool fluid, and a heating chamber external to the cavity and proximate the one surface. The cavity, surfaces and ports are formed and positioned with respect to each other so that the paths of fluid flowing substantially directly from the one surface through the optical cavity to the other surface encompass most, or preferably all, of the volume of the cavity, whereby most, or preferably all, of the cool fluid in the cavity is swept from the cavity, i.e., replaced, by the hot fluid replaces it (the cool fluid flows back out the ports in the other surface; each surface, of the two surfaces, has one or more ports). The portions of hot fluid flowing along the various flow paths through the cavity all begin to arrive at the other surface at about the same time, i.e., their leading edges or interfaces with the cool fluid ahead of them all arrive at the other surface at about the same time or phase of the cycle, whereupon, since the arrival of this "warm front" means that the replacement of the cold fluid by hot fluid in the optical cavity is basically complete or maximized, the fluid injection means terminates the injection of hot fluid and withdrawal of cool fluid (by means of the valves, for example), so that the warm front does not substantially pass through the other surface and substantially enter, and be substantially cooled by, the cooling chamber just beyond the other surface, which would waste heat if it occurred. Then, after an optional delay or dwell time of predetermined duration, which increases the amplitude of the Fourier component of the spectral signal at the fundamental frequency (the frequency of the fluid temperature modulation in the cavity) thereby improving the signal-to-noise ratio, the entire process is basically reversed, with hot fluid being withdrawn from the cavity via the ports in the one surface, flowing through the thermal regenerator for cooling (thereby storing its heat in the regenerator for use later when the fluid returns), thence through the blower and valves, through a cooling chamber proximate the other surface but external to the optical cavity, for cooling the fluid further, then through the pervious other surface as cold fluid, providing a "cold front" which sweeps substantially all of the volume of, and thus sweeps substantially all of the hot fluid from, the optical cavity by the time it reaches the one surface, i.e., arrives at the one surface, whereupon there is, optionally, another dwell of selected length, to complete the cycle. Since the fluid paths of the cold front, like those of the hot front, encompass most, or even substantially all, of the optical cavity, and since the fluid in each of the parallel paths of a given front (in the sense that the flow paths are in parallel) having leading edges, or interfaces with the fluid of different temperature ahead of it, that all arrive at the pervious surface ahead of it at approximately the same time, and since, further, there is a thermal regenerator in the recirculation circuit, with proper alternating flow through the regenerator, the present invention is more efficient, thermally and otherwise (e.g., size, weight, power requirement, cost), and is a more sensitive multigas analyzer (for reasons such as higher signal-to-noise, less possible thermal cycling of the optical cavity walls, and lower detector temperatures), than the multigas analyzer of my U.S. Pat. No. 3,836,255, which probably was potentially the most practical of my three previous gas analyzers (the devices of the three U.S. Patents mentioned above).

Since the recirculation circuit or recycling path is constantly connected to the atmosphere or other fluid medium being analyzed (except perhaps during the dwells), the temperature modulation at constant fluid pressure in the optical chamber is substantially achieved. The ports on at least one of the above-mentioned pervious surfaces are shaped and located such that most of the surface is pervious to fluid flow, in the sense that, if the at least one surface is considered as being made up of several sub-areas of roughly equal size, most of the sub-areas would each be considered pervious by virtue of containing at least a portion of a port. The at least one surface is also extended in area sufficiently to constitute a significant fraction of the internal wall area or surface area of the cavity, thereby facilitating fluid flow paths that encompass substantially all of the volume of the optical cavity, and thereby facilitating substantially complete sweeping out or replacement of a batch of fluid in the cavity twice each cycle by the alternating hot and cold fronts. The at least one surface, further, is preferably highly reflective, to at least the wavelengths of interest, in spite of the grid or array of ports or port portions distributed approximately uniformly over its surface area. Thus the port or ports (one extended port could conceivably be sufficient) in the at least one extended surface should be made as small in total area as possible consistent with facilitating adequate and properly directed flow needed for the substantially complete sweeping out and withdrawal, each cycle, of the gas filling the optical cavity.

The thermal regenerator can be formed in many different ways, e.g., stainless steel wool, metal screens, thin sheets of material. The regenerator can also serve as a particulate filter, or adsorber of undesirable chemicals or interferents. The regenerator can also be used as a catalytic converter, to chemically change interferents or other undesirable chemicals, such as chemicals that might degrade the optical cavity. By using two different types of regenerators separately, for example, one of which decomposes a substance of interest or an interferent and the other does not, and making a separate concentration measurement with each regenerator and subtracting the two, a much more accurate measurement of concentration could be made, and worth the extra effort, in certain difficult cases, using this difference method. Thus it might be worthwhile for the gas analyzer to include two or more thermal regenerators, of different types chemically, located and connected essentially in parallel in the recirculation means or recycling path, proximate the heating chamber and hot surface of the optical cavity, with the external heating chamber connected between the optical cavity and the regenerators, and further including a distributor valve for selecting one regenerator at a time, to facilitate ratio or differential measurements, such as the difference method mentioned above. One common and troublesome interferent in atmospheric, and especially in exhaust stack, measurements of chemical concentrations is water vapor and water droplets, e.g., an aerosol of water. In such a case, a thermal regenerator which could absorb or otherwise remove water from the system or from the measurement could be of great value. Of course, just the fact that this entire recycling circuit and optical chamber is kept warm by the external heat constantly applied, e.g., heat from an arc lamp or other radiant sources shining into the cavity, will in most cases be sufficient to avoid the water vapor condensation problem which sometimes occurs, since water vapor pressure increases rapidly with increasing temperature, and since, for example, the electromagnetic absorption strength of water vapor in the infrared is at least one order of magnitude (factor of ten) less than the infrared absorption strength of the same amount of liquid water in the optical path, due to the much smaller dipole moment of the $H_2O$ molecule when it is dispersed as a vapor than when it is densely associated with other water molecules as a liquid. Thus, in this gas analyzer, the waste thermal energy from the radiant sources can be utilized in at least two different ways—facilitating development of the periodic spectral radiance in the optical chamber and on the detector flakes in the presence of a gas of interest in the gaseous mixture, and secondly, substantially reducing or eliminating the condensation problem that often occurs when a warm, vaporous, supersaturated mixture or aerosol is sampled and cooled by a gas analyzer. In addition, the cooling of some radiant sources is of value in proper operation of the sources, such as an arc lamp, and can be of value in cooling certain nearby instrument components, such as radiant detectors. Thus the cooling of the radiant sources or lamps by the recirculation circuit can, all at the same time, benefit the radiant sources, proximate instrument components, the temperature modulation of the sample, the condensation problem if it occurs, and the operation of the optional chemically active thermal regenerator mentioned above, e.g., the catalytic converter/thermal regenerator. However, for most purposes, an isobaric temperature modulation amplitude of only about 100° C. would be adequate since, on a signal-to-detector noise basis, and assuming a one cubic foot gas analyzer, twenty second response time, and an ambient temperature thermal type detector, such as a pyroelectric detector, and further assuming, for the sake of simplified calculations, that there is no interference or drift, the sensitivities for various infrared absorbing (and therefore emitting) gases would typically be on the order of one part per billion, if the analyzer is properly designed. Therefore the thermal regenerator might not be hot enough to properly serve as a catalytic converter in certain cases.

From my earlier discussion of hot fronts moving uniformly across the cavity from the pervious hot surface toward (in a fluid flow sense; not necessarily a perfectly straight line but guided by the cavity walls) the pervious cold surface and converging uniformly and simultaneously (ideally) on the pervious cold surface, alternating with cold fronts sweeping uniformly across the cavity in similar fashion from the pervious cold surface to the pervious hot surface, with the fronts sweeping, and the fluid flow paths encompassing, the entire volume of the optical cavity, it follows that the entire optical chamber, including the two pervious surfaces and all the ports, should be formed and positioned relative to each other, and the conduits leading to and terminating at these ports should be aligned and formed, such that the fluid flowing through either pervious surface into the cavity via the respective ports does flow substantially directly from this surface to the opposite pervious surface, with a minimum of eddy currents, random of circuitous flow, and stagnant regions or regions of "backwash", as might occur, for example, in corners of the optical chamber or cavity. It is also preferable to form the optical chamber and its conduits and ports to avoid directing a strong or high velocity jet of fluid directly against a wall surface of the cavity, especially where there might be a substantial temperature difference between the surface and the jet of fluid, in order to minimize any undesirable thermal cycling of, and therefore cyclical infrared emission from, the wall surface in that region. However, a wall of good thermal conductivity and specific heat, such as metal, would undergo very little temperature cycling. If there is any tendency of certain chemicals to coat the walls and undergo temperature cycling, that could be handled in at least two ways. First, since the chemicals would be in liquid or solid phase, rather than gaseous phase, their molecular vibration-rotation lines would be smeared out by collision broadening, whereby they would have broad, relatively structureless bands in the near and middle infrared, which would have relatively little effect, for example, on a selective pneumatic detector, such as disclosed in U.S. Pat. No. 2,924,713, or on most any detectors utilizing proper optical filtering, especially if gas chamber filters are used, e.g., the filtering technique disclosed in my U.S. Pat. No. 3,488,491. Since thermal cycling of a possible chemical coating on a cavity wall surface, or of the wall surface itself, if either is present and of significant and troublesome magnitude, would lag the phase of the temperature modulation of the gas sample, a second method of handling a possible interference from a chemical coating, as well as possible interference from a temperature cycling wall portion, is merely using standard synchronous rectification and smoothing after a.c. amplification of the detector signal, which probably would be used anyway for greatly improving the signal-to-noise ratio by filtering out noise and drift. Since the synchronous detection is phase sensitive, the interfering signal at lagging phase would tend to be cancelled out, depending on the phase lag. The degree of cancellation increases as a phase lag increases toward 90°, and becomes virtually complete at 90°. If necessary, the desired spectral radiance signal from the gas can be synchronously rectified at a phase which leads the interference signal by 90°, whereby the interference signal from the coating or wall would be cancelled out (if present).

If desired, and if chemical coating of the cavity is not a problem, the optical chamber can be constructed to develop an out-of-phase greybody (nonspectral) signal from thermal cycling of the cavity wall surface, in order to continuously and automatically balance each analytical and reference detector pair monitoring the concentration of a gas of interest, or each pair of analytical and reference channels monitoring a gas of interest, by a synchronous rectification and nulling technique disclosed in my U.S. Pat. No. 3,516,745 (columns 5 and 6), whereby output drift can be further reduced.

It should be kept in mind when considering thermal cycling that, since the reflectivity of the cavity surface (inner surface of the optical chamber wall) is high at most wavelengths, its emissivity at the same wavelengths is low whereby, for a given temperature fluctuation, the infrared emission variation would be less than that of a blackbody. Similarly, the emissivity of a chemical coating, if present, would be less than that of a blackbody (i.e., less than unity).

Another way to handle thermal cycling, if it occurs and is undesirable, is to use an optical chopper or filter wheel operated at a frequency different from (probably higher than) the frequency of the gas sample temperature modulation. This can be helpful if common mode rejection of a large greybody signal is a limiting factor, or to more fully utilize the inherent sensitivity of a high speed detector. If, in this connection, the gas temperature modulation frequency is lowered sufficiently to produce substantially nonadiabatic conditions in the cavity, the pattern of operation of the injection means might have to be modified, as, for example, by continuing to supply hot or cold gas even after the hot or cold front reaches the pervious surface at the far end of the path through the cavity. When using two frequencies, synchronous rectification at both frequencies would generally be desirable, as discussed in my U.S. Pat. No. 3,836,255 (columns 12 and 13). The chopper or filter wheel can be located between a source and the cavity or between the cavity and a radiant detector, if shielded properly; usually a chopper is placed in front of the source. Some sources, such as arc lamps, can be chopped or pulsed electrically.

It will become evident, upon consideration of the accompanying drawings, that the above and still further objects, features and advantages are recognized and achieved to a significantly greater extent by the present invention than by the prior art.

Figure 2:
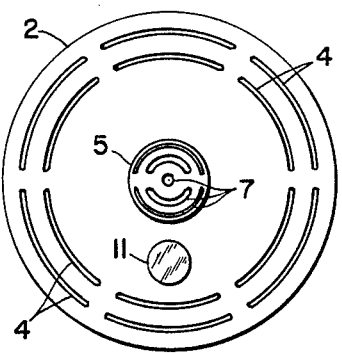
Figure 3:
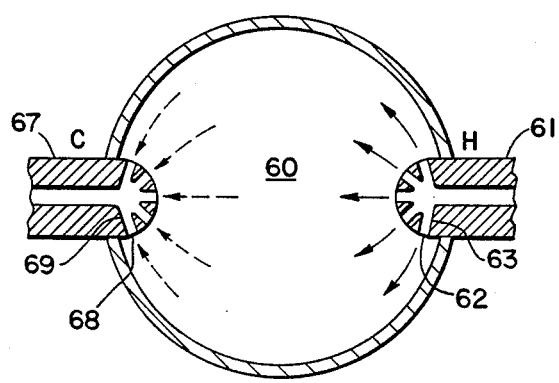
Figure 4:
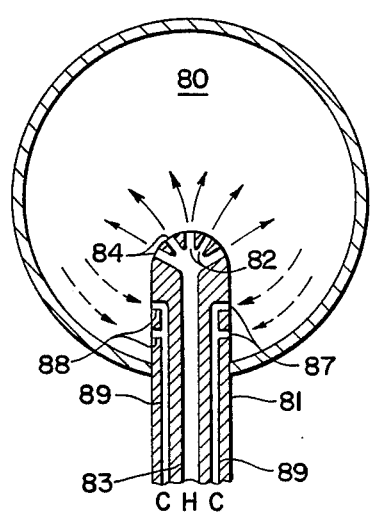

Referring now to the drawings, FIG. 1 is a cross-sectional. partly schematic illustration of one embodiment of the present invention, including an optical chamber near the top and a recirculation circuit below the optical chamber on the illustration. FIG. 2 is a view from inside the optical chamber of FIG. 1 of the hot pervious surface on the right side of the optical chamber. FIG. 3 shows a modified optical chamber, which is basically spherical in shape rather than cylindrical. FIG. 4 illustrates another alternative design for the optical cavity of the present invention, wherein the chamber is again spherical (basically) but wherein the hot and cold pervious surfaces are proximate each other on a single prong inserted into the optical chamber, rather than being on opposite sides of the cavity as in FIGS. 1 and 3.

Referring now in detail to the drawings, FIG. 1 illustrates an optical chamber or cavity 1 in the form of a right circular cylinder including a hot pervious surface 2 as its right endface and a cold pervious surface 3 as its left endface. hot surface 2 is basically a circular disc containing slit shaped ports 4 near its circumference and a sprayer 5 at the center of the disc containing short conduits 6 leading to additional hot ports 7. An arc lamp 10, including special hot, emissive material (not shown) close to the arc for emitting infrared and possibly visible radiation to augment the primarily ultraviolet radiant emission from the arc, radiates into optical cavity 1 via a window 11 in hot surface 2. Arc lamp 10 is mounted in, and provides heat for, heating chamber 14 which is external to cavity 1 and abuts the hot pervious surface 2. Optical chamber or cavity 1 is highly reflective (inside).

Cold pervious surface 3, on the opposite side of the cavity from the hot surface, includes slit-shaped cold ports 18 similar in shape to the hot ports 4 of hot surface 2. The cold surface 3 could have a cold sprayer similar to the hot sprayer 5. External cooling chamber 20, outside of the optical cavity 1 and abutting the cold surface 3, cools the gaseous fluid flowing into and out of cavity 1 via cold ports 18 in the cold pervious surface 3, and may require internal and external cooling fins (not shown) and a fan or blower (not shown), although ambient cooling of the gas analyzer case may provide sufficient cooling without the need for a separate cooling fan, especially if cooling chamber 20 is made part of the gas analyzer case, or at least connected to the case properly to promote good heat transfer to the case. Similarly, heating chamber 14 may have internal heat transfer fins (not shown) for improved heating of the gaseous fluid injected into, and withdrawn from, optical cavity 1 via ports 4 and 7 in the hot pervious surface 2, but heating chamber 14 would be thermally insulated from the ambient environment including certain instrument components. For example, the optical chamber can be constructed from several segments, such as segments 16 between the segments corresponding to the heating and cooling chambers, to provide some thermal insulation between the heating chamber and hot pervious surface on the right and the cooling chamber and cold pervious surface on the left. This insulation not only reduces the thermal, and therefore electrical, power requirement of the gas analyzer but also helps keep certain instrument components cool, such as radiant detector pair 24 and radiant detector pair 26 which are each connected to electronics box 28 utilzing synchronous detection techniques to monitor one gas of interest for each detector/filter pair. Radiant detector/optical filter pair 24 looks into optical cavity 1 via window 25 while radiant detector/optical filter pair 26 looks into the cavity through window 27. For simultaneous monitoring of many substances of interest in the gaseous sample, many filter/detector pairs can be mounted on the optical chamber walls and look into the cavity. A filter wheel can increase the number of substances monitored per detector, if desired, as well as offering other potential advantages discussed earlier, regarding possible thermal cycling and high speed detectors.

Heating chamber 14 is connected to the hot side of a recycling path or recirculation circuit 30 via thermal regenerator 34 and cooling chamber 20 is connected to the cold side of the recycling path. By means of rotary distributor valves 38 and 39, which are similar to the rotary valve 7 in my U.S. Pat. No. 3,836,255, and interconnecting conduits, a blower 40 recycles fluid alternately from the cooling chamber to the heating chamber via regenerator 34 (solid arrows show the cold fluid being recycled back to the optical cavity 1 as hot fluid injected through the hot pervious surface 2) and from the heating chamber 14 back to the cooling chamber 20 (dotted arrows show the hot fluid withdrawn from the cavity 1 flowing through the regenerator 34 and cooling chamber 20 and thus being recirculated back to the cavity as cold fluid injected into the cavity 1 via cold ports 18 in cold surface 3), with a preselected dwell between these two alternate portions of the temperature modulation cycle.

Rotary valves 38 and 39, driven by a motor (not shown), can each rotate in either direction at a frequency of rotation equal to the desired frequency of the isobaric temperature modulation of the gaseous mixture in optical cavity 1. Rotary valve 38 feeds gas upwardly toward the viewer from its single inlet below the plane of the paper, and distributes the gas either to the conduit on the right or the conduit on the left, according to whether the cutout portion 43 is to the right or to the left. Rotary valve 39 draws gas either from the conduit on its left or from the conduit on its right, according to whether its cutout portion 43 is to the left or right, and feeds the gas downwardly from the viewer to its single outlet below the plane of the paper. The conduits on the left and right of each valve have widened or funnel-shaped portions 45 where they connect to the valve body, which are optional. The optional funnel portions 45 slightly extend the portion of the cycle during which each of the four conduits is operational, thereby slightly extending and "rounding off" the injection/withdrawal portions of the temperature modulation cycle, and thus also decreasing the dwell time between the periods of fluid injection/withdrawal in optical cavity 1. The dwell times occur when the valve cutout portions are close to their midway positions between the left and right conduits where the cutout portions do not, for a short duration of time, overlap the funnel portions 45 of the conduits on the left and right. The optional "wave-shaping", by the "rounding off" and the adjustment of the duration of the dwell, can produce an approximately sinusoidal gas temperature modulation in the optical cavity, for improving the signal-to-noise ratio, and therefore the sensitivity of the fluid analyzer.

The recirculation circuit constantly communicates with the atmosphere or other fluid medium being sampled by means of inlet conduit 48, which is connected to the low pressure side of blower 40, and outlet conduit 49, which is connected to the high pressure side of the blower. Therefore, if the pressure of the atmosphere or other medium being sampled is constant, the temperature modulation of the sample in the optical chamber will be substantially at constant pressure, i.e., isobaric. The sampling conduits 48 and 49 allow the recirculation circuit to "breath out and in" as the gaseous sample is alternately heated and cooled isobarically. In other words, except for the dwells, the optical cavity and recirculation circuit are in constant communication with the fluid medium being sampled, and the sampled fluid is not being substantially heated or cooled during the dwells. Therefore the periodic temperature variation of fluid in the optical cavity, i.e., sampled fluid, occurs at substantially constant pressure if the pressure of the atmosphere or other fluid mixture being sampled is substantially constant during the temperature variation cycle.

It follows from the above description of the spectrometric substance analyzer in FIG. 1 that, alternately and isobarically, a hot front sweeps across the optical cavity from the hot surface to the cold surface and a cold front sweeps across the cavity from the cold pervious surface back to the hot pervious surface, with an optional dwell or time lag between each sweep. Thereby, the fluid in the optical cavity at the current temperature is substantially completely swept out and replaced by fluid at the new or succeeding temperature, twice each cycle, at substantially constant fluid pressure, and with a minimum of wasteful sweeping, e.g., nonuniform or multiple sweeping of the same area, or sweeping far beyond the pervious surface at the far end of the cavity (sweeping far beyond the pervious surface through which the old fluid is being withdrawn from the cavity, wherever in the optical cavity that surface, with its one or more ports, may be). Waterful sweeping degrades system performance, regarding especially power/required, sensitivity and response time.

Typically, a detector/filter pair, such as detector/filter pair 24, would have two identical detector flakes, one of which looks into the optical cavity 1 via an analytical filter which passes wavelengths of one or more characteristic absorption or emission bands (generally characteristic absorption and emission are at the same wavelengths) of the substance or gas that that detector/filter pair is supposed to monitor the concentration of, while the other detector flake looks into the cavity through a reference filter designed to transmit an equal amount of cyclical radiant energy but at nearby or reference wavelengths not characteristically absorbed or emitted by the gas of interest. The two detector flakes are typically in a bridge circuit, which, if the gas is present in the sample, produces a difference signal which is amplified and synchronously rectified at the proper phase to produce a d.c. signal, which is smoothed by an RC filter (resistance-capacitance), which smoothed d.c. signal is a measure of the concentration of the gas of interest in the sampled medium, and at low concentrations is proportional to gas concentration, as described in slightly more detail in my above-mentioned U.S. patents. If the gas of interest monitored by that detector/filter pair is not present in the sample, the difference signal and d.c. output are supposed to be zero, but spectral interferences can sometimes be a problem, and optical filters containing gases can help, especially in the infrared. A phase sensor (not shown) provides phase information to electronics box 28, so that the a.c. difference signal can be rectified at the proper phase. The phase sensor can take any of several forms, such as, for examples, a switch or relay on one of the synchronized rotary valves; a radiant detector looking into the optical cavity through a wideband optical filter; a temperature sensor such as a thermopile or thermistor disposed in the optical cavity or recirculation circuit.

Thermal regenerator 34, by containing thin pieces of material which store heat from, and release almost all of the stored heat to, the fluid flowing through the regenerator from and to the heating chamber 14 via the associated conduits of the recycling path, facilitates a greater amplitude and frequency of the periodic isobaric temperature variation of sampled gaseous fluid in optical cavity 1 for a given thermal input to the fluid in heating chamber 14 and a given rate of cooling of the fluid, primarily in cooling chamber 20. Thermal regenerators, which are designed to minimize thermal transfer through the regenerator material from the hot end to the cold end of the regenerator, are well known in the field of Stirling cycle engines and Stirling cycle cryogenic coolers, but are not known, or at least not well known, in the field of gas analyzers.

Thermal regenerators are also designed to introduce into the fluid path a minimum of additional volume and a minimum of fluid drag. This can be accomplished by providing properly designed multiple fluid flow paths arranged in parallel. One regenerator design that has been used experimentally in Stirling cycle engines is a stack of loosely wound spools or spirals of metal foil. Multiple thin plates or sheets, arranged in parallel and properly spaced, and possibly cut into segments or strips to reduce axial heat flow (parallel to the fluid flow axis), can thus serve as a decent regenerator. Radiant heat transfer should also be kept to a minimum. Because of its low infrared emissivity, metal foil serves well in this respect, too. And metal foil can take a high temperature, also.

Thermal regenerators in Stirling cycle engines have been operated satisfactorily at frequencies up to at least fifty Hertz, which is more than enough for the gas analyzer of the present invention. For even an optical chamber as small as one cubic inch, assuming its surface area-to-volume ratio is not much higher than that of a sphere, the gas temperature in the chamber, with respect to thermal losses to the chamber walls, would be substantially adiabatic at frequencies above about ten Hertz, so a larger chamber of low surface area-to-volume ratio would be substantially adiabatic at even lower frequencies, whereby a regenerator with 50 Hertz capability would be more than fast enough to accommodate a temperature modulation frequency likely to be selected for the gas analyzer of the present invention.

Of course, since phenomena special to the gas analyzer will have to be carefully considered, such as chemical adsorption, absorption and reactivity, a selected thermal regenerator design will likely be a compromise between thermodynamic considerations and the special needs of the gas analyzer of the present invention. And of course the usual practical considerations, such as cost, size, weight, reliability and lifetime, will be factors in this selection as well as for the entire gas analyzer.

FIG. 2 illustrates the hot pervious surface 2, including hot slits 4, the hot sprayer 5 containing hot slits 7, and the window 11 of radiant source 10, as viewed from the center of the optical chamber 1. The hot slits serve as hot ports of the hot pervious surface 2, and thereby serve as openings through which hot gas is injected into, and later withdrawn from, the optical cavity each cycle by the recirculation circuit or injection and withdrawal means.

FIG. 3 illustrates an alternative shape for the optical chamber, wherein the cavity now is basically spherical rather than the substantially cylindrical shape of the cavity in FIG. 1. Thus, substantially spherical, highly reflective optical cavity 60 includes a highly reflective sprayer head 61 inserted slightly into the right side of cavity 60 and serving, by virtue of hot ports 62 of hot conduits 63 within the sprayer head, as a hot pervious surface of cavity 60. Hot sprayer 61 has a convex, substantially spherical shape where it enters cavity 60 (radius of curvature much less than the general radius of curvature of cavity 60). The hot sprayer head 61 is highly reflective except, perhaps, for hot ports 62, but the hot conduits 63 can be made metallic or otherwise (the entire hot sprayer 61 can be metallic) for high reflectivity and low infrared emissivity, to help conserve the electromagnetic radiation in cavity 60 and to reduce any possible cyclical infrared emission from the hot sprayer due to possible thermal cycling of the hot conduits (unless such a signal is desired for calibration, analytical and reference channel balancing, or otherwise). The solid arrows show hot gas or other hot compressible fluid being injected into cavity 60 while cold fluid (dotted arrows) is being withdrawn from the opposite side of the cavity through cold sprayer head 67 which is inserted slightly into the left side of optical chamber 60 and is constructed similarly to the hot sprayer 61. Thus the cold fluid is withdrawn through cold ports 68 of cold conduits 69 of the cold sprayer 67 and is cooled therein or flows to a cooling chamber (not shown). Cold sprayer 67 thereby serves as the cold pervious surface of the optical cavity 60. By substantially eliminating corners, the spherical cavity 60 makes the flat disc-shaped hot and cold pervious surfaces 2 and 3, respectively, of FIG. 1 unnecessary. Thus the sprayers 61 and 67 of FIG. 3 are sufficient to efficiently sweep the fluid from the spherical optical cavity twice each cycle, in the manner discussed earlier.

FIG. 4 shows a highly reflective spherical optical cavity 80 into which is inserted a highly reflective dual sprayer head 81 containing hot conduits 82 branching out from a central, axial hot passageway 83 within the dual sprayer. The hot conduits terminate in hot ports 84 in the spherical tip of the sprayer 81, whereby the spherical tip serves as the hot pervious surface through which hot fluid (solid arrows) is injected into the optical cavity 80 while cold fluid (dotted arrows) is being swept out or withdrawn from the cavity through cold ports 87 of cold conduits 88 branching out from a cold passageway 89 running just below the cylindrical surface of the rod-shaped dual sprayer 81 in an axial direction (parallel to the axis of the rod or cylinder formed by the sprayer surface). Thus a segment of the cylindrical surface near the sprayer tip serves, by virtue of cold ports 87, as the reflective cold pervious surface of optical chamber 80. This is a very simple design, as far as the optical chamber is concerned, but thermal insulation is especially important here because of the close proximity of the hot and cool passageways and conduits. Cryogenic or Dewar techniques, such as the use of evacuated, internally reflective chambers or envelopes between the hot and cold portions of the sprayer 81, are of value in this dual sprayer design. As with FIG. 3, twice each cycle the arrows reverse. (The arrows in FIG. 1 have a different meaning; the solid and dotted arrows there represent gas flow direction during two different portions of the cycle.)

As discussed in my U.S. Pat. No. 3,836,255, it is difficult to increase the versatility of a multigas analyzer by broadening the wavelength range of a spectrometric gas analyzer to include, simultaneously, those spectral regions best suited, primarily on a sensitivity/cost/size basis, to radiant absorption techniques and those spectral regions best suited to radiant emission techniques. Generally, radiant absorption measurements are best in the ultraviolet, visible and sometimes the near infrared regions of the electromagnetic spectrum, while radiant emission measurements are best in the middle infrared and, in many cases, the near infrared. A very simple, compact and sensitive way of making the infrared emission measurements (to monitor gas concentration) is by periodic compression of a gas sample in or into a highly reflective, random path, optical chamber or cavity. The resulting periodic concentration increase and adiabatic temperature increase of the gaseous sample in the cavity combine to produce a relatively large, periodic, characteristic spectral radiant emission by the substance or gas of interest in the sample in the optical cavity, and the resulting periodic characteristic radiance in the cavity can be monitored by, for example, one or more infrared detectors looking into the cavity through infrared filters appropriate to the gas of interest, whereby, using synchronous rectification, the concentration of the substance of interest in the sampled gaseous medium may be continuously monitored in real time, and recorded or displayed. Various techniques for accomplishing this periodic compression of gas samples and infrared monitoring of the gas of interest are disclosed in my U.S. Pat. Nos. 4,110,618; 4,063,094; and 3,516,745.

If, however, with such an analyzer, one attempts to cover more gases of interest or cover them better by extending the spectral coverage to shorter wavelengths, such as into the ultraviolet, by increasing the compression ratio, one generally finds that thermal decomposition of gases of interest, especially organic molecules, as well as pumping and other instrumentation problems, limit the wavelength extension to the near infrared. If, alternatively, one attempts the wavelength extension toward shorter wavelengths by shining infrared, visible and ultraviolet sources into the optical cavity, with the intent to monitor the modulated radiant absorption by the gases of interest resulting from their periodic concentration variation in the optical cavity, one finds that this can work well in the ultraviolet, visible, and possibly the near infrared portions of the electromagnetic spectrum bu that, in the near and middle infrared, a periodic infrared emission signal is present at the characteristic infrared absorption, and therefore emission, wavelengths of the substances of interest present in the gas sample, as a result of the periodic temperature variation of these substances in the sample, due to the periodic, substantially adiabatic, compression of the gaseous sample in the optical cavity. The periodic infrared emission signal is in phase with the periodic infrared absorption signal, but the two signals are of opposite polarity (as far as the infrared detector is concerned), so they tend to cancel each other (their rectified output signals are of opposite polarity and therefore subtract), thereby reducing sensitivity of the gas analyzer in the infrared. Due to the difference in the blackbody curves at the gas temperature and at the much higher radiant source temperature, and due also to the relatively small size of the radiant source as compared with the size of the optical cavity (e.g., on a surface area basis, weighted by emissivity), the infrared emission signal gradually becomes larger, and the infrared absorption signal gradually becomes smaller, as the wavelengths of observation are shifted from the visible toward longer wavelengths in the infrared. Thereby, the canceling increases toward longer wavelengths and the sensitivity decreases, until, at a crossover wavelength in the infrared, the amplitudes of the periodic emission and the periodic absorption are equal, whereby the cancelation is complete and the sensitivity is zero. At wavelengths longer than the crossover wavelength, the emission signal predominates over the absorption signal, and the sensitivity gradually climbs back up. But over a substantial spectral interval including, and extending on each side of, the crossover wavelength, the sensitivity of such a gas analyzer would not be adequate for most purposes.

The location of the crossover wavelength, at which sensitivity is zero, depends on instrument parameters, but would typically be in the near or middle infrared, both valuable spectral regions for detecting and monitoring gases of interest. If one attempts to solve the canceling problem by increasing the radiant power of the radiant source in the infrared, which will shift the crossover wavelength to longer wavelengths of the infrared, the increased size, weight, power requirement and cost of the radiant source, as well as the increased heat load from the now powerful radiant source make the instrument less desirable and practical, especially as a portable multigas analyzer, and especially also when taken in conjunction with the already substantial power requirement of the pump or compressor needed for the cyclical compression of the sample.

It was primarily to greatly broaden the spectral range of coverage of a practical, portable multigas analyzer that the device of my U.S. Pat. No. 3,836,255 was invented, and the present invention achieves this also, since both inventions utilize periodic temperature variation of a gaseous sample at constant pressure in a highly reflective optical cavity, which eliminates the canceling problem and facilitates substantial reduction of the pumping and other practical instrument problems mentioned above. The isobaric temperature modulation does cause the gas concentration to be at a minimum in the optical cavity at the time of maximum gas temperature and desired maximum infrared emission by the gas of interest, which drop in concentration does reduce the number of molecules of the gas of interest which can contribute to the infrared emission at this time or phase of the cycle, thereby reducing the amplitude of the spectral infrared emission signal that otherwise could have been generated in the optical cavity had the same amplitude of temperature modulation occurred without the inverse concentration modulation, but, due to the nonlinearlity of the blackbody curve with respect to temperature, the temperature factor is much more important than the concentration factor in determining infrared emission from a gas, so that the periodic spectral infrared emission by the gas of interest in the optical cavity is more than strong enough, in spite of the concentration varying inversely with the gas temperature at constant pressure, to facilitate the high sensitivity discussed above. In other words, in the infrared, and especially in the near and middle infrared, e.g., $1-15 \times 10^{-6}$ meters in wavelength (usually $0.72-3.0 \times 10^{-6}$ meters is considered the near infrared; $3.5-20 \times 10^{-6}$ meters the intermediate or middle infrared; and $20-1000 \times 10^{-6}$ meters the far infrared region), the radiant emission from a gas at very low concentrations (which is when sensitivity is so important) varies with the first power of (linearly with) gas concentration, while the radiant emission varies much faster than this with gas temperature (a power much greater than unity). Thus, in a constant pressure system, the radiant emission is in phase with the gas temperature variation and, in spite of the gas concentration varying at 180° out-of-phase with respect to the temperature variation, the periodic spectral emission signals by the gases of interest in the optical cavity typically are large enough in amplitude to permit, on a signal-to-detector noise basis, part-per-billion detection of many gases of interest simultaneously, in real time, by a practical, portable, multigas analyzer, assuming that the instrument is properly designed. To this end, for example, the optical cavities in FIGS. 1, 3 and 4 (optical cavities 1, 60 and 80, respectively), including the hot plate 2 and hot sprayer 5 in FIG. 2, are made as highly reflective (internally, of course) as possible and practical, considering the ports, the spectral range of the gas analyzer, and the chemical stability needed for the material of the surfaces of the optical cavities. But if the instrument is built properly, the inherent high sensitivity of the random path optical chamber, with its long effective optical path length (many times its diameter) and with its relatively large quantity of gas sample within it, facilitates sensitive, simultaneous monitoring of many substances of interest in a gaseous medium, in almost real time (relatively short response time) by a practical, rugged, portable device which is a multigas analyzer in the full sense of one device being able to sensitively detect and monitor the concentrations of virtually any gases of interest in a complex gaseous mixture, in a practical, economical way. At least that is the primary goal of the present invention.

Generally, but depending on instrument parameters (especially the nature of the radiant sources selected, and the temperature range of the gas sample temperature modulation), the periodic emission signal by the gaseous sample predominates over its periodic absorption signal in the middle and far infrared (the far infrared is seldom used for these purposes, primarily because of low sensitivity and strong atmospheric interferences, e.g., by water vapor and carbon dioxide; but an emission type gas analyzer, such as the present invention, is better able to use the far infrared than a portable spectrometric gas analyzer not utilizing infrared emission by the sample), while the periodic radiant absorption predominates over the periodic radiant emission by the sample in the ultraviolet and visible and perhaps in the near infrared. But no matter in what spectral region the periodic emission and absorption signals by the gas are simultaneously present in the optical cavity, the two signals add rather than subtract from each other, since, in this isobaric temperature modulation system, the two signals are 180° out of phase (one half cycle out of phase) and of opposite polarity. Thereby, in spectral regions common to both periodic emission and periodic absorption of electromagnetic radiant energy by the gaseous sample in the optical cavity, the emission and absorption signals are phased to augment each other, in algebraic fashion, rather than subtracting and tending to cancel each other, as would be the case if unchopped (unmodulated) radiant sources were used in conjunction with a compressive type gas sample modulation system (chopped radiant sources would avoid the canceling problem but would require double synchronous rectification, i.e., at the chopping frequency and again at the gas sample compression frequency, an additional complication and cost; and compressive type pumps generally introduce pumping type problems, such as vibration, lifetime, servicing power requirement, size, weight, cost and, especially in the case of a piston type compressor, possible generation of unwanted, undesirable radiant signals at the gas compression frequency, e.g., by the changing geometry). Therefore the present invention facilitates relatively high gas analyzer sensitivity throughout the ultraviolet, visible and infrared regions of the spectrum, except for regions of strong interference by constitutents of the gaseous sample, and limited, of course, by the availability of suitable optical, electrical and mechanical components and materials - but these appear to be available.

As disclosed in U.S. Pat. No. 3,319,071, a random path optical cavity should not be perfectly spherical but should be randomized by distortions, such as dimples in the spherical surface while still maintaining high reflectivity of the surface. The randomization minimizes normal modes of reflection which never reach the filter/detector pair window and thus can not contribute to the sensitivity of the gas analyzer. The randomization increases the effective optical path length of the cavity to a value which can be many times the cavity diameter, depending mainly on reflectivity and port and window areas in addition to the randomization, and can increase the radiant signal power at the detectors. In the present invention, the hot and cold sprayers serves as randomizers, in addition to their other function of facilitating the proper injection and withdrawal of hot and cold gas, respectively (hot sprayers inject and withdraw hot gas and cold sprayers inject and withdraw cold gas, into and from the cavity). But dimples can be added if desired (to the surfaces of the substantially spherical cavities 60 and 80 in FIGS. 3 and 4, respectively).

In view of all the above, it should be evident that the present invention, to a significantly greater extent than the prior art, facilitates the difficult task of building a practical, portable, sensitive, truly multigas analyzer in the fullest sense.

It should also be evident, especially to those skilled in the art, that numerous modifications and variations of the embodiments of the present invention specifically described herein can obviously be made that would still fall within the above teachings and within the scope of the appended claims.

It should further be evident that the present invention can also be used as an oscillatory pressure source, e.g., as in my burglar alarm patents, U.S. Pat. Nos. 3,968,482; 3,990,069 and 3,990,063; or as a combined burglar and gas detector (burglar, gas and fire alarm, if products of combustion are detected).

What is claimed as new and desired to be secured by Letters Patent of the United States is:

1. A radiant emission and absorption gas analyzer comprising a cavity reflective to electromagnetic radiation, said cavity including first and second wall surfaces pervious to fluid flow through said surfaces, said surfaces each containing one or more ports through which fluid can pass into and back out of the cavity, means for injecting fluid at a first average temperature into the cavity through said first surface while withdrawing fluid from the cavity through said second surface, then injecting fluid at a second average temperature into the cavity through said second surface while withdrawing fluid from the cavity through said first surface, means for cyclically repeating the sequence of said injections at approximately said first and second average temperatures, and further including detector means responsive to the cyclical variation in spectral electromagnetic radiance in the cavity resulting from the presence of a substance of interest in the fluid and the cyclical injections of fluid at approximately said first and second average temperatures into the cavity; the ports of said first surface being shaped and located on said first surface such that most of the first surface is pervious to fluid flow, said first surface constituting a significant fraction of the internal wall area of the cavity and being reflective to electromagnetic radiation in the cavity; said injecting means including means for maintaining a substantially constant fluid pressure in the cavity during the cycle.

2. A gas analyzer as in claim 1, said cavity and said surfaces and all said ports being formed and positioned with respect to each other such that the paths of fluid flowing substantially directly from said first surface to said second surface during the first said injection encompass most of the volume of the cavity.

3. A gas analyzer as in claim 2, said cavity, said surfaces and all said ports further being formed and positioned such that the paths of fluid flowing substantially directly from said second surface to said first surface during the second said injection of the cycle encompass most of the volume of the cavity.

4. A gas analyzer as in claim 1, said cavity, said surfaces and all said ports being formed and positioned so that most of the fluid injected through said first surface arrives at said second surface at approximately the same time.

5. A gas analyzer as in claim 4 wherein said injecting means includes means for stopping the first said injection each cycle at the approximate arrival time of said fluid at said second surface.

6. A gas analyzer as in claim 4 wherein said cavity, surfaces and ports are formed and positioned such that most of the fluid injected into the cavity through said second surface arrives at said first surface at approximately the same time during the second said injection.

7. A gas analyzer as in claim 6 wherein said injecting means includes means for stopping the second said injection each cycle at approximately the approximate arrival time of said fluid at said first surface.

8. A gas analyzer as in claim 1 wherein the injecting means includes means for introducing a dwell time of preselected duration between each of said injections.

9. A gas analyzer as in claim 1 further including fluid recirculation means for utilizing some of the withdrawn fluid as injected fluid each cycle, whereby at least some of the fluid injected through said surfaces each cycle is derived from fluid previously withdrawn from the cavity.

10. A gas analyzer as in claim 9 wherein said fluid recirculation means includes a thermal regenerator.

11. A gas analyzer as in claim 10 further including a heated source producing radiation for said cavity and supplying heat to recirculating fluid flowing out of said thermal regenerator toward one of said pervious wall surfaces.

12. A gas analyzer as in claim 1 further including fluid recirculation means for utilizing some of the withdrawn fluid as injected fluid each cycle, whereby at least some of the fluid injected through said first and second surfaces each cycle is derived from fluid withdrawn through said second and first surfaces, respectively, less than one-half cycle previous to its re-injection back into the cavity.

13. A gas analyzer as in claim 12 wherein said fluid recirculation means includes a thermal regenerator.

14. A gas analyzer as in claim 1 wherein said first and second pervious wall surfaces are disposed on approximately opposite sides of said reflective cavity.

15. A gas analyzer as in claim 1 wherein the ports of said second surface are shaped and located on said second surface such that most of the second surface is pervious to fluid flow, said second surface constituting a significant fraction of the internal wall area of the city and being reflective to electromagnetic radiation in the cavity.

16. A gas analyzer as in claim 1 wherein one of said previous wall surfaces is disposed at least partially on a projection extending into said cavity.

17. A gas analyzer as in claim 1 further including a radiant source emitting electromagnetic radiation into said cavity, said source supplying heat to fluid being injected through one of said surfaces into the cavity.

18. A gas analyzer as in claim 1 further including sampling means facilitating, during most of the cycle, communication between fluid in the gas analyzer and a body of fluid external to the gas analyzer.

19. A gas analyzer as in claim 18 further including a blower, both said injection means and said sampling means including said blower.

20. A gas analyzer as in claim 19 wherein said injection and withdrawal means further includes, in series between said pervious wall surfaces, a heating means, a thermal regenerator means, and a cooling means for recycling withdrawn fluid as injected fluid alternately through said first and second pervious wall surface, whereby the resulting cyclical heating and cooling of sampled fluid in the gas analyzer produces a cyclical and alternating fluid flow between the gas analyzer and said external body of fluid via said sampling means in approximate synchronism with the alternate and cyclical heating and cooling of sampled fluid in the gas analyzer.

21. A monitoring device which samples a gaseous fluid and cyclically modulates the temperature of the sampled fluid comprising an internally reflective chamber including a hot port means and a cold port means; injection means for alternately and cyclically injecting hot and cold sampled fluid into said reflective chamber via said hot and said cold port means, respectively, while withdrawing primarily cold and primarily hot fluid, respectively from the reflective chamber; a heating chamber for heating fluid being injected into the reflective chamber as hot fluid; a cooling chamber for cooling fluid being injected into the reflective chamber as cold fluid; said injection means including a recirculation means disposed externally to said reflective chamber and connecting said hot and said cold port means in a fluid flow relationship, said injection means further including means for inducing fluid flow in said recirculation means in alternate directions between said hot and said cold port means.

22. A monitoring device as in claim 21 wherein one of said port means includes multiple ports through which fluid is simultaneously injected into the reflective chamber.

23. A monitoring device as in claim 22 wherein the other port means also includes multiple injection ports.

24. A monitoring device as in claim 21 wherein one of said port means includes at least one port having a length much greater than its width.

25. A monitoring device as in claim 21 wherein said hot and said cold port means each include at least one port having a length much greater than its width.

26. A monitoring device as in claim 21 wherein one of said port means is disposed at least partially on a convex pervious wall surface of said reflective chamber.

27. A monitoring device as in claim 26 wherein the other port means is disposed at least partially on another convex pervious wall surface of the reflective chamber.

28. A monitoring device as in claim 21 wherein said cold port means is disposed on and forms a cold pervious wall surface of said reflective chamber, said cold pervious wall surface constituting a significant fraction of the wall area of said reflective chamber.

29. A monitoring device as in claim 28 wherein said hot port means is disposed on and forms a hot pervious wall surface of said reflective chamber, said hot pervious wall surface constituting a significant fraction of the wall area of said reflective chamber.

30. A monitoring device as in claim 21 wherein said internally reflective chamber, said hot and said cold port means, and said injection means are designed so that said injected hot sampled fluid forms a hot front which traverses most of the volume of the reflective chamber as it moves from said hot port means to, and converges substantially simultaneously on, said cold port means.

31. A monitoring device as in claim 30 wherein said reflective chamber, said hot port means, said cold port means, and said injection means are designed such that said injected cold sampled fluid forms a cold front which traverses most of the volume of said reflective chamber as it moves from said cold port means to, and converges substantially simultaneously on, said hot port means.

32. A monitoring device as in claim 31 further including dwell means for substantially stopping the injection of fluid during first and second selected dwell portions of the cycle beginning at the end of the hot and cold injections, respectively, said first and second dwell portions selected to begin approximately when said hot front reaches said cold port means and approximately when said cold front reaches said hot port means, respectively.

33. A monitoring device as in claim 21 wherein said injection means and one of said port means include sprayer means for deflecting through a range of angles the gaseous fluid being injected via that port means into the reflective chamber.

34. A monitoring device as in claim 21 wherein said hot port means includes hot sprayer means, and said cold port means includes cold sprayer means, for directing through a range of angles the hot gaseous fluid and the cold gaseous fluid being injected into the reflective chamber via said hot port means and said cold port means, respectively.

35. A monitoring device as in claim 21 wherein said inducing means includes two valves operated synchronously with each other.

36. A monitoring device as in claim 21 wherein a portion of said recirculation means includes two fluid-conducting branches arranged, but not operated, in parallel with each other.

37. A monitoring device as in claim 36 wherein each of said branches includes a three-way valve, the two valves being operated synchronously with each other.

38. A monitoring device as in claim 36 wherein said recirculation means further includes a third fluid-conducting branch connecting said two fluid-conducting branches.

39. A monitoring device as in claim 38 wherein said inducing means includes a blower disposed in said third fluidconducting branch.

40. A monitoring device as in claim 39 further including two sampling conduits connected to said recirculation means on opposite sides of said blower.

41. A monitoring device as in claim 36 further including thermal regenerator means disposed in said recirculation means at a location between said fluid-conducting branches and said hot port means.

42. A monitoring device as in claim 21 further including thermal regenerator means disposed in said recirculation means so as to be subjected to the fluid flow in said alternate directions.

43. A monitoring device as in claim 21 wherein said hot port means includes one or more hot ports disposed at or near the tip of a probe projecting into said reflective chamber.

44. A monitoring device as in claim 21 further including radiant detector means mounted so as to be responsive to a cyclical spectral variation in electromagnetic radiance in said reflective chamber resulting from the temperature modulation of the sampled fluid.

45. A monitoring device as in claim 21 further including means for maintaining the pressure of the sampled fluid in the monitoring device substantially constant throughout substantially all of the temperature modulation cycle.

46. A monitoring device as in claim 21 further including sampling means connected to said recirculation means for sampling of the gaseous fluid by the monitoring device.

47. A monitoring device as in claim 21 further including sampling conduit means providing, during the hot and cold injections, substantially constant communication between the sampled fluid in the reflective chamber and the body of gaseous fluid being sampled by the monitoring device.

48. A monitoring device as in claim 21 wherein the primarily cold fluid being withdrawn from the reflective chamber is withdrawn at least primarily via said cold port means.

49. A monitoring device as in claim 48 wherein the primarily hot fluid being withdrawn from the reflective chamber is withdrawn at least primarily via said hot port means.

50. A monitoring device as in claim 21 wherein the primarily hot fluid being withdrawn from the reflective chamber is withdrawn at least primarily via said hot port means.

51. A monitoring device which cyclically modulates the temperature of a gaseous fluid comprising an internally reflective chamber including a hot port means and a cold port means, and injection and withdrawal means for cyclically and repeatedly (a) injecting hot sampled fluid into the chamber via said hot port means while withdrawing fluid from a portion of the chamber proximate said cold port means, and, immediately or soon thereafter, (b) then injecting cold sampled fluid into the chamber via said cold port means while withdrawing fluid from a portion of the chamber proximate said hot port means; said injection and withdrawal means including recirculation and temperature modification means for recirculating a substantial portion of the withdrawn fluid in (a) and (b) back into said chamber as injected fluid, said recirculation and temperature modification means including a thermal regenerator for alternately and cyclically storing heat from withdrawn hot fluid in (b) and releasing stored heat to withdrawn cold fluid in (a).

52. A monitoring device as in claim 51 wherein said injection and withdrawal means includes means for withdrawing cold fluid from the chamber via said cold port means during (a) and hot fluid from the chamber via said hot port means during (b).

53. A monitoring device as in claim 51 wherein said cold port means includes one or more cold ports extending or distributed over a cold pervious internal surface of the chamber, said cold pervious surface representing a significant fraction of the internal surface area of the chamber.

54. A monitoring device as in claim 53 wherein said hot port means includes one or more hot ports extending or distributed over a hot pervious internal surface of the chamber, said hot pervious surface representing a significant fraction of the internal surface area of the chamber.

55. A monitoring device as in claim 51 wherein said hot port means includes multiple hot ports disposed on a hot pervious internal wall surface of the chamber, and wherein said injection and withdrawal means includes multiple hot injection conduits terminating in said hot ports, most of said hot injection conduits being angled with respect to each other proximate said hot ports.

56. A monitoring device as in claim 55 wherein said cold port means includes multiple cold ports disposed on a cold pervious internal wall surface of said chamber, and wherein said injection and withdrawal means includes multiple cold injection conduits terminating in said cold ports, most of said cold injection conduits being angled with respect to each other proximate said cold ports.

57. A monitoring device as in claim 51 wherein said cold port means includes multiple cold ports disposed on a cold pervious internal wall surface of said chamber.

58. A monitoring device as in claim 57 wherein said injection and withdrawal means including multiple cold injection conduits terminating in said cold ports, most of said cold injection conduits being angled with respect to each other proximate said cold ports.

59. A monitoring device as in claim 57 wherein said hot port means includes multiple hot ports disposed on a hot pervious internal wall surface of said chamber.

60. A monitoring device as in claim 59 wherein said hot and cold pervious surfaces have disparate locations on the wall of said chamber.

61. A monitoring device as in claim 59 wherein said hot and cold pervious surfaces are approximately on opposite sides of said chamber.

62. A monitoring device as in claim 51 wherein said hot port means includes multiple hot ports disposed on a hot pervious internal wall surface of said chamber.

63. A monitoring device as in claim 51 wherein said recirculation and temperature modification means includes fluid conductors arranged on parallel but respective segments thereof operated serially.

64. A monitoring device as in claim 51 wherein said hot port means is at least partially disposed on a substantially convex surface of said chamber as viewed from within the chamber.

65. A monitoring device as in claim 51 wherein said hot port means is disposed on a substantially convex surface of said chamber as viewed from within the chamber.

66. A monitoring device as in claim 51 wherein said hot port means is disposed at least primarily at or near the tip of a projection projecting into said chamber.

67. A monitoring device as in claim 66 wherein said projection is substantially rod-shaped.

68. A monitoring device as in claim 51 further including means for maintaining a substantially constant fluid pressure in said chamber during the cycle.

69. A monitoring device as in claim 51 further including conduit means for maintaining, during (a) and (b), substantially constant communication between the sampled fluid in said chamber and an external body of fluid being sampled by said device.

70. A monitoring device as in claim 51 further including conduit means maintaining, throughout the cycle, substantially constant fluid flow communication between sampled fluid in said device and a body of fluid external to the device and being monitored by a device.

71. A monitoring device as in claim 70 wherein said conduit means includes two sampling conduits, one providing a net inward flow of fluid into said device from said external body of fluid, the other providing a net outward flow of fluid from said device to said external body of fluid.

72. A monitoring device as in claim 71 wherein said injection and withdrawal means includes a blower, said two sampling conduits being connected to basically opposite sides of said blower.

73. A monitoring device as in claim 51 wherein said injection and withdrawal means further includes dwell means between (a) and (b) and (b) and (a) each cycle, during typical operation of the device.

74. A monitoring device as in claim 51 further including a source supplying electromagnetic radiation to said internally reflective chamber and suppying waste heat to the hot sampled fluid being injected into said chamber during (a).

75. A monitoring device as in claim 74 further including cooling means for cooling the sampled fluid being injected into the chamber during (b).

76. A monitoring device as in claim 75 wherein said cooling and said waste heat are supplied to the sampled fluid on opposite sides of said thermal regenerator in said recirculation and temperature modification means.

77. A monitoring device as in claim 75 further including radiant detector means responsive to a cyclical and spectral variation in electromagnetic radiance in said chamber resulting from the temperature modulation of the gaseous sampled fluid.

78. A monitoring device as in claim 69 further including radiant detector means responsive to a cyclical and spectral variation in electromagnetic radiance in said chamber resulting from the temperature and concentration modulation of the gaseous sampled fluid.

79. A monitoring device as in claim 51 further including radiant detector means for monitoring a cyclical and spectral radiant emission and/or absorption by the sampled gaseous fluid in said internally reflective chamber.

80. A monitoring device as in claim 79 wherein said radiant detector means includes at least one radiant detector/optical filter pair responsive to cyclical spectral electromagnetic radiation emanating from said chamber.

81. A monitoring device which cyclically modulates the temperature of a gaseous fluid comprising an internally reflective chamber including a hot port means and a cold port means, and injection and withdrawal means for cyclically and repeatedly (a) injecting hot sampled fluid into the chamber via said hot port means while withdrawing fluid from a portion of the chamber proximate said cold port means, and, immediately or soon thereafter, (b) injecting cold sampled fluid into the chamber via said cold port means while withdrawing fluid from a portion of the chamber proximate said hot port means; said injection and withdrawal means including recirculation and temperature modification means for recirculating a substantial portion of the withdrawn fluid in (a) and (b) back into the chamber as injected fluid during (a) and (b), respectively.

82. A monitoring device as in claim 81 further including means for accomplishing the temperature modulation of the gaseous fluid substantially isobarically.

83. A monitoring device as in claim 81 wherein said injection and withdrawal means includes means for withdrawing cold fluid from the reflective chamber via said cold port means during (a) and hot fluid from the chamber via said hot port means during (b).

84. A monitoring device as in claim 81 wherein said injection and withdrawal means includes hot sprayer means and cold sprayer means for injecting the respective hot and cold gaseous fluids into the chamber over a range of angles.

85. A monitoring device as in claim 81 wherein said hot port means includes multiple hot ports and said cold ports means includes multiple cold pots.

86. A monitoring device as in claim 81 wherein said hot and said cold port means and said injection and withdrawal means are disposed and designed such that the injected hot and the injected cold sampled fluids form hot and cold fronts, respectively, which fronts, during (a) and (b), tranverse most of the volume of the reflective chamber as they move substantially directly toward, and converge substantially simultaneously on, said portions of the chamber proximate said cold and said hot port means, respectively.

87. A monitoring device as in claim 81 further including dwell means for, between (a) and (b) and/or between (b) and (a) of the cycle, substantially stopping the injection of fluid into the reflective chamber.

88. A monitoring device as in claim 81 further including conduit means facilitating, during (a) and (b), substantially constant communication between the sampled fluid in said chamber and a body of gaseous fluid external to the monitoring device.

89. A monitoring device as in claim 81 wherein said recirculation and temperature modification means includes a thermal regenerator.

90. A monitoring device as in claim 81 further including radiant source means emitting electromagnetic energy into said reflective chamber.

91. A monitoring device as in claim 81 further including radiant detector means responsive to cyclical, spectral, electromagnetic radiation emanating from said reflective chamber. in synchronism with the temperature modulation of the gaseous sampled fluid.

92. A monitoring device as in claim 81 further including a source supplying electromagnetic radiation to said internally reflective chamber and also supplying waste heat to, and thereby being cooled by, the hot gaseous sampled fluid being injected into said chamber during (a).

93. A monitoring device as in claim 81 further including a source producing electromagnetic radiation emission into said internally reflective chamber, said source also providing heat for heating gaseous fluid being injected into said chamber as how sampled fluid.

94. A monitoring device as in claim 93 further including means for maintaining the pressure of the sampled fluid in said reflective chamber substantially constant throughout substantially all of the temperature modulation cycle.

95. A monitoring device as in claim 94 further including means for detecting spectral electromagnetic radiation emanating from said reflective chamber in synchronism with the temperature modulation and the substantially inverse concentration modulation of the gaseous sampled fluid in said chamber.

96. A monitoring device as in claim 95 wherein said recirculation and temperature modification means includes a thermal regenerator.

97. A monitoring device as in claim 96 wherein said internally reflective chamber, said hot port means, said cold port means, and said injection and withdrawal means are designed such that most of the cold sampled fluid in the chamber is replaced by hot sampled fluid during (a) and most of the hot sampled fluid in the chamber is replaced by cold sampled fluid during (b).

98. A monitoring device as in claim 94 wherein said recirculation and temperature modification means includes a thermal regeneration.

99. A monitoring device as in claim 98 wherein said internally reflective chamber, said hot port means, said cold port means, and said injection and withdrawal means are designed such that most of the cold sampled fluid in the chamber is replaced by hot sampled fluid during (a) and most of the hot sampled fluid in the chamber if replaced by cold sampled fluid during (b).

100. A monitoring device as in claim 99 wherein the fluid withdrawn from said portion of the chamber proximate said cold port means during (a) is withdrawn from the chamber at least primarily via said cold port means.

101. A monitoring device as in claim 100 wherein said cold port means includes one or more cold ports distributed over, and thereby forming, a cold pervious surface through with cold pervious surface cold sampled fluid is injected into said internally reflective chamber during (b) and primarily cold sampled fluid is withdrawn from said chamber during (a), said cold pervious surface representing a significant fraction of the internal surface area of said chamber.

102. A monitoring device as in claim 101 wherein the fluid withdrawn from said portion of the chamber proximate said hot port means during (b) is withdrawn from the chamber at least primarily via said hot port means.

103. A monitoring device as in claim 102 wherein said hot port means includes one or more hot ports distributed over, and thereby forming a hot pervious surface through which hot pervious surface hot sampled fluid is injected into said internally reflective chamber during (a) and primarily hot sampled fluid is withdrawn from said chamber during (b), said hot pervious surface representing a significant fraction of the internal surface area of said chamber.

104. A monitoring device as in claim 81 wherein said cold port means includes one or more cold ports distributed over, and thereby forming, a cold pervious surface through which cold pervious surface cold sampled fluid is injected into said internally reflective chamber during (b) and primarily cold sampled fluid is withdrawn from said chamber during (a), said cold pervious surface representing a significant fraction of the internal surface area of said chamber.

105. A monitoring device as in claim 104 wherein said hot port means includes one or more hot ports distributed over, and thereby forming, a hot pervious surface through which hot pervious surface hot sampled fluid is injected into said internally reflective chamber during (a) and primarily hot sampled fluid is withdrawn from said chamber during (b), said hot pervious surface representing a significant fraction of the internal surface area of said chamber.

106. A monitoring device comprising a chamber internally reflective to electromagnetic radiation, said chamber including a first and a second injection conduit means terminating, respectively, at a first and a second port means disposed on the internal surface of said chamber, an injection means for first injecting sampled faseous fluid at a first average temperature into said chamber through said first port means via said first injection conduit means while withdrawing gaseous fluid from a portion of said chamber proximate said second port means, and immediately or soon thereafter, during a second injection injecting sampled gaseous fluid at a second average temperature into said chamber through said second port means via said second injection conduit means while withdrawing gaseous fluid from a portion of said chamber proximate said first port means, said injection means including means for alternately and cyclically repeating the first and second injections of sampled gaseous fluid at said first and second average temperature; said chamber, said first injection conduit means, said first port means and said second port means being designed such that the sampled gaseous fluid cyclically injected into said chamber at said first average temperature is injected into the chamber over a range of substantially different first injection angles directing the injected gaseous fluid in first, injection paths leading substantially directly, though not necessarily in a perfectly straight line, to said portion of the chamber proximate said second port means, said substantially direct first injection paths, taken as a group, encompassing most of the internal volume of said chamber.

107. A monitoring device as in claim 106 wherein the gaseous fluid withdrawn from said portion of the chamber proximate said second port means is withdrawn from said chamber at least primarily via said second port means.

108. A monitoring device as in claim 107 wherein the gaseous fluid withdrawn from said portion of the chamber proximate said first port means is withdrawn from said chamber at least primarily via said first port means.

109. A monitoring device as in claim 106 wherein said first and said second port means are disposed at separate and substantially disparate locations on, i.e., in separate and substantially disparate regions of, said internal surface of said chamber.

110. A monitoring device as in claim 106 wherein said first and said second port means are disposed substantially at opposite sides or opposite ends of said chamber.

111. A monitoring device as in claim 106 wherein said chamber, said second injection conduit means and said second and said first port means are designed such that the sampled gaseous fluid cyclically injected into said chamber at said second average temperature is injected into the chamber over a range of substantially different second injection angles directing the injected fluid in second injection paths leading substantially directly, though not necessarily precisely in a straight line, to said portion of the chamber proximate said first port means, said substantially direct second injection paths together encompassing most of the internal volume of said internally reflective chamber.

112. A monitoring device as in claim 111 wherein said injection means includes a recirculation and temperature modification means including a thermal regeneration.

113. A monitoring device as in claim 112 further including a sampling means for obtaining said sampled gaseous fluid.

114. A monitoring device as in claim 111 wherein the gaseous fluid withdrawn from said portion of the chamber proximate said second port means is withdrawn from said chamber substantially entirely via said second port means.

115. A monitoring device as in claim 114 wherein the gaseous fluid withdrawn from said portion of the chamber proximate said first port means is withdrawn from said chamber substantially entirely via said first port means.

116. A monitoring device as in claim 115 wherein said first port means includes one or more first ports distributed over, and thereby helping to form, a first pervious surface through which first pervious surface said sampled fluid at, i.e., averaging, said first average temperature is injected into said chamber during said first injection, and also through which first pervious surface fluid primarily at approximately said first average temperature is withdrawn from the chamber during said second injection, said first pervious surface representing a significant fraction of the internal surface area of said chamber.

117. A monitoring device as in claim 116 wherein said injection means includes a recirculation and temperature modification means including a thermal regenerator.

118. A monitoring device as in claim 117 further including a sampling means maintaining, during said first and second injections, fluid flow communication between said chamber and a body of fluid external to said device.

119. A monitoring device as in claim 116 wherein said second port means includes one or more second ports distributed over, and thereby helping to form, a second pervious surface through which second pervious surface sampled fluid averaging said second average temperature is injected into said chamber during said second injection, and also through which second pervious surface sampled fluid primarily averaging approximately said second average temperature is withdrawn from the chamber during said first injection, said second pervious surface representing a significant fraction of the internal surface area of said chamber.

120. A monitoring device as in claim 119 wherein said injection means includes a fluid recirculation and temperature modification means including a thermal regenerator.

121. A monitoring device as in claim 120 wherein said injection means includes a means for maintaining the pressure of the sampled gaseous fluid in said chamber substantially constant during substantially the entire (or the entire) cycle of said injections.

122. A monitoring device as in claim 115 wherein said injection means includes a recirculation and temperature modification means including a thermal regenerator.

123. A monitoring device as in claim 111 wherein said first port means includes one or more first ports distributed over, and thereby helping to form, a first pervious surface through which first pervious surface sampled fluid averaging said first average temperature is injected into said chamber during said first injection, and also through which first pervious surface fluid primarily at approximately said first average temperature, i.e., primarily fluid averaging approximately said first average temperature, is withdrawn from the chamber during said second injection, said first pervious surface representing a significant fraction of the internal surface area of said chamber.

124. A monitoring device as in claim 123 wherein said second port means includes one or more second ports distributed over, and thereby helping to form, a second pervious surface through which second pervious surface sampled fluid averaging said second average temperature is injected into said chamber during said second injection, and also through which second pervious surface sampled fluid primarily averaging approximately said second average temperature is withdrawn from the chamber during said first injection, said second pervious surface representing a significant fraction of the internal surface area of said chamber.

125. A monitoring device as in claim 124 wherein said injection means includes a recirculation and temperature modification means including a thermal regenerator.

126. A monitoring device as in claim 123 wherein said injection means includes a recirculation and temperature modification means including a thermal regenerator.

127. A monitoring device as in claim 113 wherein said sampling means includes means for maintaining a substantially constant fluid pressure in said chamber during the cycle of said alternate first and second injections.

128. A monitoring device as in claim 111 further including a means for sampling fluid from an external body of fluid and for substantially equalizing the fluid pressures in said body and said chamber throughout the cycle.

129. A monitoring device as in claim 126 wherein the temperature variations of the sampled fluid in said device are substantially isobaric.

130. A monitoring device as in claim 125 wherein the temperature variations of the sampled fluid in said device are induced substantially isobarically.

131. A monitoring device as in claim 115 wherein the resulting fluid temperature variation in said chamber is substantially isobaric.

132. A monitoring device as in claim 108 further including a substantially regenerative, substantially isobaric, sampled fluid recirculation and sampling means for facilitating substantially isobaric operation of said device.

133. A monitoring device as in claim 107 further including a substantially regenerative, substantially isobaric, fluid recirculation and sampling means facilitating said first and second injections at substantially atmospheric pressure.

134. A monitoring device as in claim 108 wherein said injection means includes a recirculation and temperature modification means including a thermal regenerator.

135. A monitoring device as in claim 134 further including a means for maintaining fluid flow communication between an external body of fluid and said chamber or said recirculation and temperature modification means throughout at least substantially all of the cycle of said injections.

136. A monitoring device as in claim 107 further including a recirculation means including a thermal regenerator for facilitating said first and second injections.

137. A monitoring device as in claim 136 further including a connecting means providing fluid flow communication between sampled fluid in said device and an external body of fluid.

138. A monitoring device as in claim 137 wherein said connecting means includes means for connecting said body of fluid to two different portions of said device having slightly different average pressures of the fluid, whereby one of said two different portions becomes a net inlet for fluid for said device and the other of said two different portions becomes a net outlet for fluid from said device even though the fluid flow between each of said two different portions and said body of fluid is substantially oscillator or cyclical to some degree.

139. A monitoring device as in claim 106 wherein said injection means includes a recirculation and temperature modification means including a thermal regenerator.

140. A monitoring device as in claim 107 further including means for maintaining substantially constant fluid flow communication between fluid in said device and an external body of fluid.

141. A monitoring device as in claim 107 further including a means for making fluid pressure in said chamber substantially isobaric.

142. A monitoring device as in claim 139 further including a means for connecting sampled fluid in said recirculation and temperature modification means to an external body of fluid, whereby the pressures of the connected sampled fluid and said body of fluid are substantially equalized during the cycle.

143. A monitoring device as in claim 142 wherein said connecting means connects said body of fluid to two different locations of sampled fluid in said device, at least one of which locations is in said recirculation and temperature modification means, said two different locations having slightly different average pressures of the sampled fluid.

144. A monitoring device as in claim 143 wherein both of said locations are in said recirculation and temperature modification means.

145. A monitoring device as in claim 106 further including a means for maintaining a substantially constant pressure of the sampled fluid in said device during a typical cycle.

146. A monitoring device as in claim 106 further including a means for inducing the fluid temperature variations in said chamber substantially isobarically during a typical cycle of said injections and withdrawals.

147. A monitoring device as in claim 106 further including a connecting means for maintaining constant fluid flow communication between sampled fluid in said device and an external body of fluid during a typical cycle of said first and second injections.

148. A monitoring device as in claim 147 wherein said connecting means connects said body of fluid to two different locations of sampled fluid in said device, said two different locations having slightly different mean fluid pressures during a typical cycle, i.e., during said typical cycle.

149. A monitoring device as in claim 106 wherein said chamber and said first and second injection and withdrawal means are designed such that, at a typical point in said chamber, a hot fluid "front" passes through said point followed by a cold fluid "front" passing through said point, said hot and cold fluid fronts cyclically and alternately passing through said typical point during typical operation of said device.

150. A monitoring device as in claim 149 wherein said device is further designed such that the characteristic direction in which the hot fronts typically pass through said typical point is typically substantially different than the characteristic direction in which the cold fronts typically and alternately pass through the same said typical point.

151. A monitoring device as in claim 150 wherein said characteristically different directions of the hot and cold fronts are approximately opposite in direction at said typical point, and thus at most points in said chamber.

152. A device for cyclically and substantially isobarically modulating gaseous fluid temperature comprising a chamber including a hot port means and a cold port means; a hot injection means, including said hot port means, for injecting hot gaseous fluid into said chamber, via said hot port means, in hot gaseous fluid injection paths leading, at least eventually, toward said cold port means; a cold injection means, including said cold port means, for injecting cold gaseous fluid into said chamber, via said cold port means, in cold gaseous fluid injection paths leading, at least eventually, toward said hot port means; means for cyclically and alternately activating said hot and said cold gaseous fluid injection means while withdrawing previously injected, mostly cold and mostly hot gaseous fluid from the chamber, at least substantially via said cold and said hot port means, respectively; said device being designed such that said hot injection paths, taken as a first group, and said cold injection paths, taken as a second group, each encompass most of the volume of said chamber; whereby most points within the chamber are cyclically and alternately traversed by a hot front moving in one direction and a cold front moving in approximately the opposite direction; said hot front and said cold front each possibly including gaps, the instantaneous total gap area of either front typically representing less than one-half of the instantaneous total area of the given front.

153. A device as in claim 152 further including a regenerative heat storage and release means facilitating the gaseous fluid temperature modulation.

154. A device as in claim 152 further including a substantially regenerative recirculation and temperature modification means facilitating said fluid temperature modulation.

155. A device as in claim 154 further including a connecting means providing fluid flow communication means between said recirculation and temperature modification means and an external body of fluid.

156. A device as in claim 155 wherein said connecting means connects said body of fluid with sampled fluid in two different portions of said recirculation and temperature modification means, said two different portions having slightly different average fluid pressures during typical cycle.

* * * * *